(12) United States Patent
Whitcher et al.

(10) Patent No.: US 8,460,361 B2
(45) Date of Patent: Jun. 11, 2013

(54) MANUFACTURING MEDICAL DEVICES BY VAPOR DEPOSITION

(75) Inventors: Forrest D. Whitcher, Allston, MA (US);
Makoto Takeuchi, Newton, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1994 days.

(21) Appl. No.: 11/180,165

(22) Filed: Jul. 13, 2005

(65) Prior Publication Data

US 2006/0000715 A1    Jan. 5, 2006

Related U.S. Application Data

(63) Continuation of application No. 10/242,382, filed on Sep. 12, 2002, now Pat. No. 6,938,668, which is a continuation of application No. 09/490,613, filed on Jan. 25, 2000, now abandoned.

(51) Int. Cl.
*A61F 2/06* (2006.01)

(52) U.S. Cl.
USPC ........................................... 623/1.15

(58) Field of Classification Search
USPC ............................ 623/1.15, 1.18–1.2, 23.53
See application file for complete search history.

(56) References Cited

U.S. PATENT DOCUMENTS

| | | | |
|---|---|---|---|
| 3,247,579 A | 4/1966 | Cattermole et al. | |
| 3,560,350 A | 2/1971 | Mattia | |
| 3,586,609 A | 6/1971 | Jansen | |
| 3,660,177 A * | 5/1972 | Brown et al. | 148/677 |
| 3,952,334 A | 4/1976 | Bokros et al. | |
| 4,038,703 A | 8/1977 | Bokros | |
| 4,351,695 A | 9/1982 | Hieber et al. | |
| 4,574,451 A | 3/1986 | Smashey et al. | |
| 4,666,442 A | 5/1987 | Arru et al. | |
| 4,800,100 A | 1/1989 | Herbots et al. | |
| 4,932,974 A | 6/1990 | Pappas et al. | |
| 5,016,808 A | 5/1991 | Heil, Jr. et al. | |
| 5,030,329 A | 7/1991 | Haidle et al. | |
| 5,064,681 A | 11/1991 | Berry et al. | |

(Continued)

FOREIGN PATENT DOCUMENTS

| | | |
|---|---|---|
| DE | 1452370 | 3/1969 |
| EP | 0400947 | 12/1990 |

(Continued)

OTHER PUBLICATIONS

Kajiwara et al., "A New Strengthening Method of sputter-Deposited Ti-Ni Shape memory Thin films," SMST-97: Proceedings of the Second International Conference on Shape Memory and Superelastic Technologies, Pacific Grove, California, U.S.A. 1997, pp. 155-160.

(Continued)

*Primary Examiner* — Bruce E Snow
(74) *Attorney, Agent, or Firm* — Fish & Richardson P.C.

(57) ABSTRACT

A method of forming a medical device, the method including the steps of providing a substrate, depositing a metallic layer on the substrate by a vapor deposition process, and removing the metallic layer from the substrate. The metallic layer thus removed is the medical device or serves as a basis for forming the medical device. In another aspect, the present invention includes a medical device formed by the process of the present invention.

8 Claims, 7 Drawing Sheets

U.S. PATENT DOCUMENTS

| | | |
|---|---|---|
| 5,118,524 A | 6/1992 | Thompson et al. |
| 5,152,774 A | 10/1992 | Schroeder |
| 5,158,750 A | 10/1992 | Finicle |
| 5,207,706 A | 5/1993 | Mennaker |
| 5,258,022 A | 11/1993 | Davidson |
| 5,320,800 A | 6/1994 | Siegel et al. |
| 5,328,587 A | 7/1994 | Fenske |
| 5,329,514 A | 7/1994 | Eguchi et al. |
| 5,352,266 A | 10/1994 | Erb et al. |
| 5,352,512 A | 10/1994 | Hoffman |
| 5,370,078 A | 12/1994 | Kou et al. |
| 5,370,684 A | 12/1994 | Vallana et al. |
| 5,376,463 A | 12/1994 | Bak et al. |
| 5,433,797 A | 7/1995 | Erb et al. |
| 5,454,886 A | 10/1995 | Burrell et al. |
| 5,468,562 A | 11/1995 | Farivar et al. |
| 5,492,763 A | 2/1996 | Barry et al. |
| 5,514,349 A | 5/1996 | Parker et al. |
| 5,532,495 A | 7/1996 | Bloomquist et al. |
| 5,543,019 A | 8/1996 | Lee et al. |
| 5,609,629 A | 3/1997 | Fearnot et al. |
| 5,611,871 A | 3/1997 | Yoshizawa et al. |
| 5,626,691 A | 5/1997 | Li et al. |
| 5,681,575 A | 10/1997 | Burrell et al. |
| 5,690,670 A | 11/1997 | Davidson |
| 5,772,864 A | 6/1998 | Moller et al. |
| 5,780,119 A | 7/1998 | Dearnaley et al. |
| 5,798,042 A | 8/1998 | Chu et al. |
| 5,847,385 A | 12/1998 | Dresch |
| 5,872,357 A | 2/1999 | Flanagan |
| 5,892,083 A | 4/1999 | Winter et al. |
| 5,894,133 A | 4/1999 | Armini |
| 5,936,513 A | 8/1999 | Rosen et al. |
| 5,937,318 A | 8/1999 | Warner, Jr. et al. |
| 6,043,451 A | 3/2000 | Julien et al. |
| 6,059,714 A | 5/2000 | Armini et al. |
| 6,096,175 A | 8/2000 | Roth |
| 6,238,686 B1 | 5/2001 | Burrell et al. |
| 6,267,782 B1 | 7/2001 | Ogle et al. |
| 6,379,383 B1 | 4/2002 | Palmaz et al. |

FOREIGN PATENT DOCUMENTS

| | | |
|---|---|---|
| EP | 0442303 | 8/1991 |
| JP | 2000/8187 | 11/2000 |
| WO | WO 97/07257 | 2/1997 |
| WO | WO 99/35312 | 7/1999 |
| WO | WO 00/04204 | 1/2000 |

OTHER PUBLICATIONS

Noort, Titanium: the implant material of today, Journal of Materials Science, vol. 22, pp. 3801-3810, Nov. 1987.

Chumlyakov et al., *Superelasticity During the Elastic Twinning, Slip and Martensitic Transformations*, Siberian Physical Technical Institute, 1, pp. 106.

Zuhr et al., *Direct Formation of Thin Films and Epitaxial Overlayers at Low Temperatures Using a Low-Energy (10-500 eV) Ion Beam Deposition System*, Materials Resarch Science, Symposium Spring MRS-1987, Anahiem, California, U.S.A., pp. 1-9.

Chumlyakov et al., *Aging Influence on the Shape Memory Effects and Superelasticity in Titanium-Nickel Single Crystals*, Materials Research Society Symposium held Dec. 1996, Boston, Massachusetts URS-56, pp. 1-6.

Kohl, M et al., "*Thin Film Shape Memory Microvalves With Adjustable Operation Temperature*," Sensors and Actuators A, CH, Elsevier Sequoia S.A. Lausanne, vol. 83, No. 1-3, May 2000 pp. 214-219, EXP004198317 ISSN: 0924-4247 paragraphs 0002, 0003.

Patents Abstracts of Japan, vol. 2000, No. 1, Jan. 31, 2000 & JP 11 267462A (Hitachi Ltd., Laser Atom Separation Eng Res Assoc of Japan), Oct. 5, 1999 abstract.

R.C. Weast et al., *CRC Handbook of Chemistry and Physics*, 1981, CRC Press, Inc., US XP002165669 pp. B-255, B-264, B-276 and B-313.

Database WPI, Section CF, *Week 197627 Derwent Publications Ltd.*, London, GB; An 1976-50558X, XP002165670 & JP 51 055724A (Tokuriki Shoten GOS), May 17, 1976 abstract.

* cited by examiner

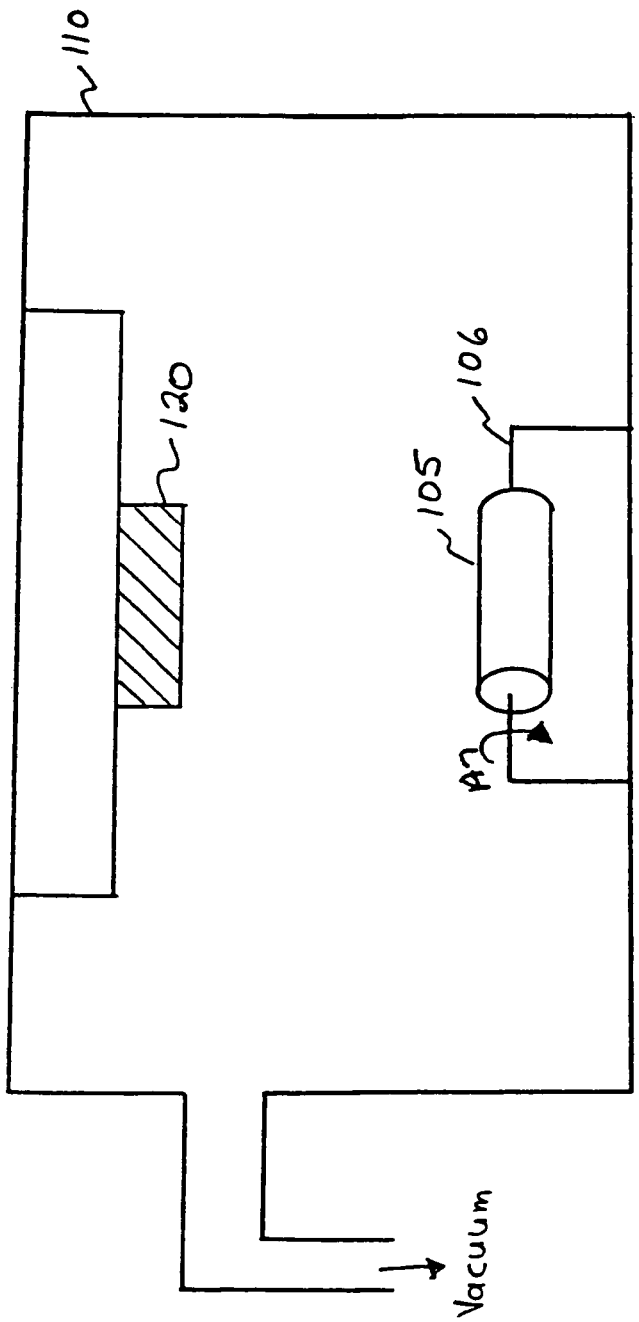

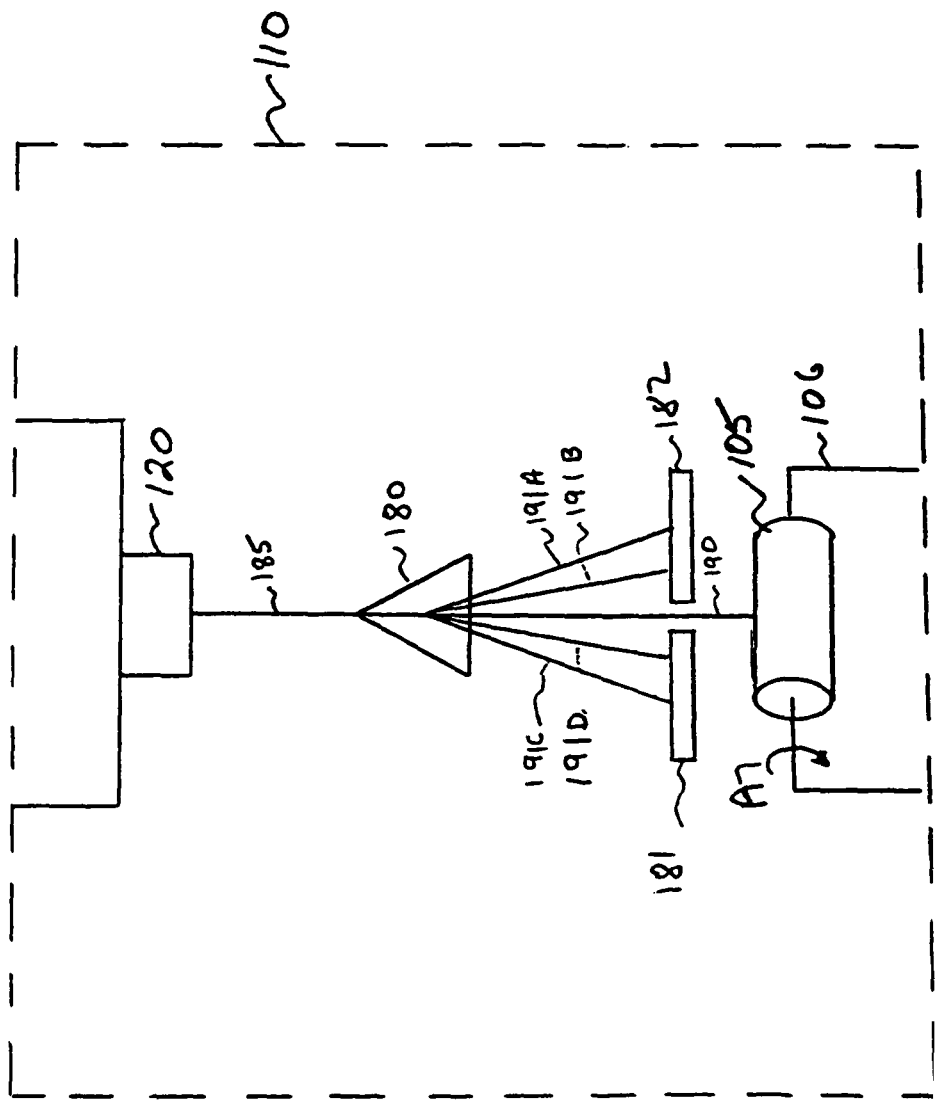

MANUFACTURING MEDICAL DEVICES BY VAPOR DEPOSITION

CROSS-REFERENCE TO RELATED APPLICATIONS

This application is a continuation application of and claims priority to U.S. application Ser. No. 10/242,382, filed on Sep. 12, 2002, now U.S. Pat. No. 6,938,668 which is a continuation application of and claims priority to U.S. application Ser. No. 09/490,613, filed on Jan. 25, 2000 now abandoned. Both applications are hereby incorporated by reference.

FIELD OF THE INVENTION

The present invention relates to medical devices and, more particularly, to medical devices having improved mechanical properties that are formed using vapor deposition techniques.

BACKGROUND OF THE INVENTION

Implantable medical devices such as stents, blood filters, artificial heart valves and the like are typically subjected to hostile working conditions. For example, stents and blood filters are introduced into the body while in a compressed shape and are thereafter expanded via self expansion or mechanical expansion to a final, useful shape when positioned to a target location within the body. After deployment, the devices should have sufficient physical, biological and mechanical properties to perform throughout the expected useful lifetime. Moreover, implantable medical devices are typically characterized by complex, intricate shapes and strict dimensional and compositional tolerances.

In view of the stringent requirements of medical devices, the processes used to form these devices must be accurate and reproducible, and obtain the desired dimensional, compositional and mechanical properties. Conventional production processes, however, are often complex and expensive. For example, conventional processes used to produce patterned stents often start with wire, tube or sheet materials. Typical processing steps to produce a patterned stent from a wire may include winding the wire around a mandrel into a complex configuration, welding the wire at certain junctions, and heat treating the wire to create the final patterned device. To produce a patterned stent from a tube or sheet, conventional processes may include steps such as stamping, cutting or etching a pattern into the starting material, expanding and/or rolling the starting material into a suitable stent shape, and heat treating to create the final device.

Most of the manufacturing steps associated with these conventional methods introduce defects into the metallic structure of the formed device. The defects can include excessive oxidation, localized deformation, surface flaws and the like. These defects often reduce desired properties, such as strength, fatigue resistance and corrosion resistance.

The performance properties of the medical device are not only effected by manufacturing processes, but are also effected by the material properties of the raw material. For instance, if the wire or tube used to form a medical device contains material or structural defects, the formed medical device may also often contain similar or greater defects. Some defects in the formed device may be reduced by techniques, such as annealing, but these techniques often impart other undesirable effects. For instance, annealing often requires high temperature treatment of a metallic device to recrystallize its microstructure to reduce grain size and residual stress. Such a high temperature treatment can often impart physical deformation of the device due to thermal heating and cooling steps or due to the change in the microstructure itself. Because medical devices often require intricate shapes and strict dimensional tolerances, physical deformation of the device during manufacturing is often a problem.

Furthermore, the compositional properties of the raw material used to form the medical device also effects the final properties of the device. Impurities often degrade useful mechanical properties, reduce corrosion resistance and effect the biocompatability of the medical device.

Accordingly, a need exists for a manufacturing process to form a medical device without the disadvantages of the prior art. Furthermore, a need exists for a medical device with improved biocompatability and mechanical properties.

In view of the shortcomings of conventional medical device manufacturing processes, there exists a need for a process that facilitates the reproducible production of medical devices having improved mechanical properties.

SUMMARY OF THE INVENTION

In one aspect, the present invention provides a method of forming a medical device, the method including the steps of providing a source of biocompatible metal; providing a substrate; depositing a biocompatible metallic layer on the substrate from the source by a vapor deposition process; and removing the metallic layer from the substrate. The metallic layer thus removed is the medical device or serves as a basis for forming the medical device.

In another aspect, the present invention includes a medical device formed by the process of the present invention. The medical devices have at least one or more members formed from biocompatible metals.

The medical devices also have a crystallographic structure that is produced by the vapor deposition methods of the present invention. Desirable crystallographic structures include amorphous, nanocrystalline and monocrystalline structures. Furthermore, the medical devices may include monoisotopic metal or alloys of monoisotopic metals.

BRIEF DESCRIPTION ON THE DRAWINGS

FIG. 4A shows an example of a vapor deposition apparatus in accordance with an embodiment of the present invention.

FIG. 4B shows the vapor deposition apparatus of FIG. 4A with mass analysis ans separation in accordance with an embodiment of the present invention.

DETAILED DESCRIPTION OF THE INVENTION

The present invention overcomes many of the difficulties associated with conventional medical devices and the methods used to form such medical devices. By using vapor deposition techniques for the formation of medical devices, the composition, thickness, surface roughness, and microstructure of devices formed in accordance with the present invention are accurately and precisely controlled. The medical devices formed by the process of the present invention are tailored to have desired compositions, mechanical properties, and geometries.

Figure 1:
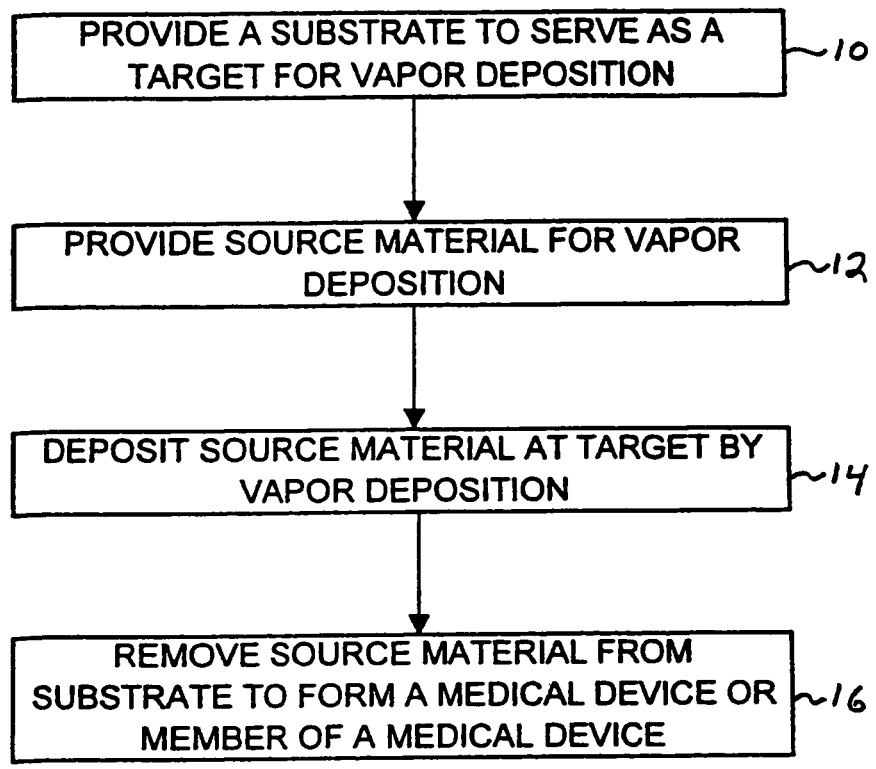
FIG. 1 shows a schematic of a method for forming a medical device according to a vapor deposition method of the present invention.

In one aspect as illustrated in FIG. 1, the present invention is directed to a method of forming a medical device, the method including the steps of providing a substrate and source material, depositing a metallic layer of source material on the substrate by a vapor deposition process, and removing the metallic layer of source material from the substrate.

At step 10, a substrate is provided to serve as a target for source material by vapor deposition. As described further herein, the material of the substrate and the configuration of the substrate are selected according to the desired aspects of the medical device or medical member formed by the process of the present invention.

At step 12, a source material for vapor deposition is provided. Desirably, the source material is biocompatible material, as described further herein, suitable for use as a medical device.

At step 14, source material is deposited as a metallic layer at the target or onto the substrate by a vapor deposition process.

At step 16, the metallic layer from the substrate is removed. The metallic layer thus removed is the medical device or serves as a basis for forming the medical device. In another aspect, the present invention includes medical devices made by the process of the present invention.

"Vapor deposition," as used herein, refers to any process of depositing metals and metal compounds from a source to a substrate or target by dissipating metal ions from the source in a vaporous medium. Examples of useful vapor deposition processes for use in the present invention include physical vapor deposition processes such as evaporation, and sputtering. Direct and assisted ion beam deposition, and chemical vapor deposition are also useful. These useful vapor deposition processes are generally described below.

In the evaporation process, vapor is generated by heating (e.g., by electron beam interaction) a source material to a temperature to cause the vaporization thereof. The evaporating metal atom leaves the surface of the source material in a straight line. Therefore, highest quality deposition layers are deposited when the source-to-substrate distance is less than the mean path distance between collisions of the vaporized metal and the surrounding vacuum chamber. At chamber pressures greater than $10^{-1}$ Pa, a useful source-to-substrate distance is generally less than 500 mm. At $10^{-2}$ Pa, this distance can be increased to over 4000 mm. Furthermore, it is useful to rotate or translate the substrate within the suitable source-to-substrate distance to ensure that the entire surface of the substrate is coated. Deposition rates using commercially available equipment typically exceed 0.05 mm per minute.

In the sputtering process, a source is bombarded with ions of an inert gas to cause the dislodgment of material therefrom. The source of ions is typically an ion beam or plasma discharge. In this technique, a source material is placed in a vacuum chamber with a substrate material. The chamber is evacuated to $10^{-3}$-$10^{-5}$ Pa, and backfilled with an inert gas such as argon to a pressure of 0.1-10 Pa to sustain a plasma discharge. The substrate is made positive, relative to the source material, by a radio-frequency power source. When the applied potential reaches the ionization energy of the gas, electrons, generated at the cathode, collide with the gas atoms, ionizing them and creating a plasma. These positively charged ions, having high kinetic energy, are accelerated toward the cathode source material, thus dislodging atoms that then travel across the electrode gap. These dislodged atoms are then deposited onto the substrate. Because of the energy of these atoms, their adherence to the substrate is generally better than if they were deposited by vacuum evaporation.

Ion beam assisted deposition (IBAD) utilizes a high energy beam of heavy ions to help densify the deposited metals, such as metals deposited by sputtering or evaporation processes. A useful ion beam assisted deposition method further includes mass analysis of the ion beam before the ionized source material is deposited onto the substrate. This method accelerates the ion beam and passes it through a filter typically containing magnetic and/or electrostatic fields to separate different mass-weight species. This filter is often referred to as an ExB filter and is commercially available. Those of skill in the art can select an ExB filter with desirable features to be useful with the present invention. A particular mass-weight species is then targeted at the substrate. When the ion sources are individual pure element ingots, this technique can be used to separate the isotopes of an element and to direct a particular isotope to the substrate. Because naturally occurring elements typically consist of a range of atomic weights or isotopes (See Table 1 below), this method is useful in selecting a particular isotope for forming a medical device. For instance, titanium with atomic weight of 48 may be selected for vapor deposition while rejecting titanium with atomic weights of 46, 47, 49 and 50. Furthermore, other impurities, such as oxygen, that may be contained in the elemental ingot may be filtered away from the substrate with this method.

TABLE 1

Naturally Occurring Isotopes of Ti & Ni

| Element | Atomic No. | Atomic Weight | Natured Occurrence % |
|---|---|---|---|
| Titanium ($_{22}Ti^{47.96}$) | 22 | 46 | 7.9 |
| | | 47 | 7.3 |
| | | 48 | 73.9 |
| | | 49 | 5.5 |
| | | 50 | 5.4 |

TABLE 1-continued

Naturally Occurring Isotopes of Ti & Ni

| Element | Atomic No. | Atomic Weight | Natured Occurrence % |
|---|---|---|---|
| Nickel ($_{28}Ni^{58.7}$) | 28 | 58 | 67.8 |
|  |  | 60 | 26.2 |
|  |  | 61 | 1.2 |
|  |  | 62 | 3.7 |
|  |  | 64 | 1.1 |

The removal of impurities and the filtering of particular isotopes are useful in the present invention. The crystalline structure of the metallic medical article may be affected by impurities. Single crystal or monocrystalline materials are more easily formed when levels of impurities are minimized. Furthermore, medical devices formed as a monocrystalline, monoisotopic material are useful with the present invention.

Large, single crystals of metals can be grown by a number of methods. One simple method is to melt the metal in a conical vessel, and then lower the vessel slowly from the furnace, point first. Under controlled temperature conditions a single seed forms at the point of the cone and continues to grow until it fills the cone or unit crystal growth is otherwise terminated. The single crystal may also slowly be drawn from the vessel as to make a filament of a single crystal. Impurities in the vessel often terminate single crystal growth. Nevertheless, a single crystal filament or write may suitable be formed. The present invention, however, is not limited to "melting" techniques for forming single crystals and other methods may suitable be used.

Such a single crystal filament or wire may then be used as a substrate in a vapor deposition process. Ionized metal atoms deposit on this substrate and may form the same crystalline structure, i.e., monocrystalline structure, as contained in the substrate. Ion beam deposition with mass analysis is a useful vapor deposition process to form monocrystalline medical devices because impurities and mass-species can be controlled. In such a manner a monoisotopic, monocrystalline medical article, such as a stent or a stent wire, may suitably be formed.

Another useful method of the present invention for forming medical devices is crystallization of structures formed with an amorphous morphology. An amorphous metallic structure may be deposited onto a substrate by vapor deposition when the substrate is a dissimilar material from the deposited material. The amorphous structure may subsequently be treated or aged under conditions that are well below typical annealing temperatures, such as about or near room temperature, to form a monocrystalline metallic structure. Ion beam deposition method is useful because impurity levels can be substantially reduced as compared to other methods. Reduced impurity levels facilitate the growth of single crystals. Moreover, monocrystalline and monoisotropic crystals can be suitably formed by vapor deposition methods, especially by ion beam depositions with mass analysis.

Furthermore, as compared to conventional processes, enhanced mechanical properties for medical devices can be obtained by minimizing the grain size of the metallic structure. Conventional grain sizes are on the order of ten microns or larger. A medical device with a nanocrystalline structure is useful because of its enhanced mechanical properties, for instance fatigue resistance and corrosion resistance. A nanocrystalline structure in a biocompatible material with a grain size ranging from about 1 to 500 nanometers is useful as a medical device. Also useful is a biocompatible material with a grain size of about 1 to 100 nanometers. Furthermore, a nanocrystalline structure in a biocompatible material with a grain size of about 1 to 50 nanometers is useful as a medical device. Moreover, a biocompatible material with a grain size of about 1 to 10 nanometers is also useful as a medical.

Such nanocrystalline structures can be formed by depositing an amorphous layer of desired material onto a substrate or target. The above-described aging techniques can be used to form nanometer sized crystals. Furthermore, the orientation of the nanometer sized grains can be controlled to yield a orderly grain structure with substantially similar crystal orientation. A useful method for forming such structures is through epitaxy where desired material is deposited onto a substrate having a crystalline structure, such as an orientated, nanocrystalline structure, and the deposited material forms a crystalline structure similar to that of the substrate.

The present invention is described with reference to the formation of a metallic stent, although it should be understood that the process of the present invention can be used to form any applicable medical device such as, for example, blood filters and artificial heart valves. Furthermore, the medical devices of the present invention have at least one or more metallic members. These members have discrete dimensions and shapes as desired for particular medical devices and for particular medical applications.

Various stent types and stent constructions may be employed in the invention. Examples of the various stents include, without limitation, self-expanding stents and balloon expandable stents. The stents may be capable of radially contracting, as well, and in this sense can be best described as radially or circumferentially distensible or deformable. Self expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals.

The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular slotted stents are also useful in the present invention.

Figure 2:
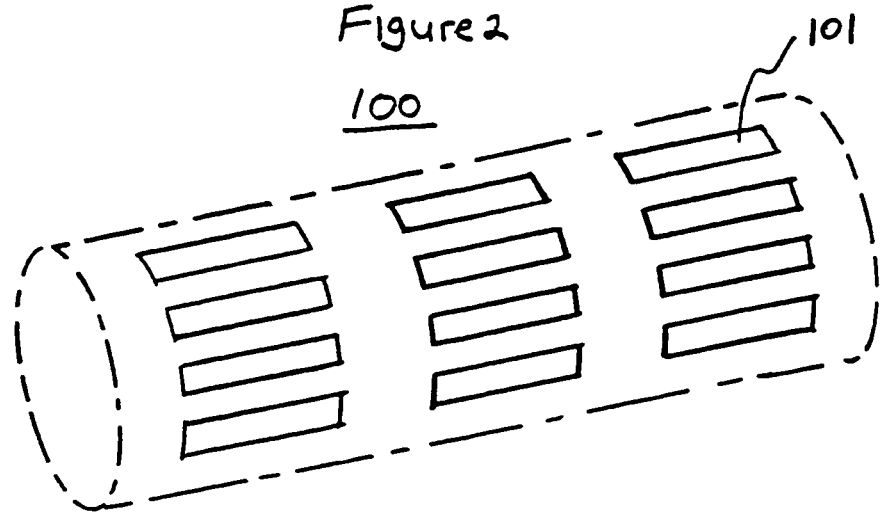
FIG. 2 shows a medical device formed according to a vapor deposition method of the present invention.
Figure 3:
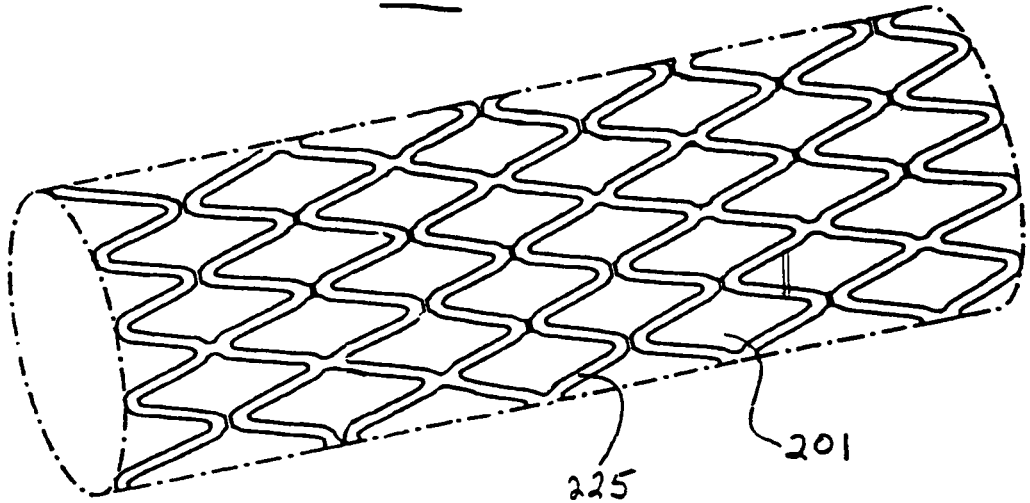
FIG. 3 shows a second medical device formed according to a vapor deposition method of the present invention.

In one aspect of the present invention, a metallic stent, such as a slotted metallic stent 100 as depicted in FIG. 2 or a wire-framed metallic stent 200 as depicted in FIG. 3, is formed according to an embodiment of the present invention. As depicted in FIG. 4A, a mandrel 105 is placed a vacuum chamber 110 or other suitable device for vapor deposition processes. The mandrel 105 is, for example, a metallic wire or any other suitable cylindrical element.

Figure 5:
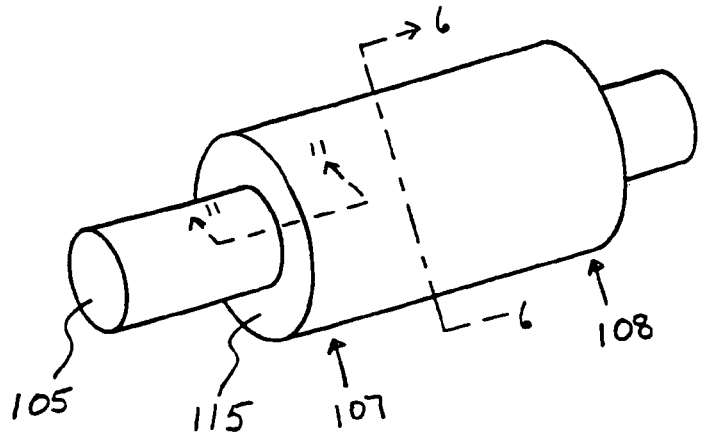
FIG. 5 shows a substrate having a deposition layer, in accordance with an embodiment of the present invention.

The mandrel 105 is desirably mounted onto a motor driven rotary mount 106 to assist in the production of a uniform deposition. During deposition, the rotary mount 106 rotates, as depicted by vector A, at a speed determined by the medical device equipment and process parameters, for instance about 1-60 rev/min. After forming an appropriate vacuum pressure in the chamber 110, the vapor deposition process commences whereby a metallic layer 115 is deposited onto the mandrel 105 as shown in FIG. 5. The source of the material deposited as the metallic layer 115 is source material 120 that is placed the vacuum chamber 110. The vapor deposition process continues until the metallic layer 115 achieves a desired thickness. As described by the aforementioned vapor deposition techniques, metallic laser 115 can be formed to have a range of crystalline morphologies, including a monocrystalline or a nanocrystalline morphology.

Metallic layer 115 may also be formed as having a monoisotopic morphology through use of mass analysis of an ion beam before the ionized source material is deposited as metallic layer 115. As depicted in FIG. 4B, vacuum chamber 110 may further include filter 180 and templates 181 and 182, interrelated as shown. Filter 180 may be used to separate the isotopes of an element or contaminants that may be present in source material 120. Desirable filter 180 is a filter containing magnetic and/or electrostatic fields, such as an ExB filter. Templates 181 and 182 are useful for targeting a particular isotope toward mandrel 105 while preventing other isotopes or contaminants from reaching mandrel 105. For example, as depicted in FIG. 4B, beam 190 contains a particular isotope of source material 120 to be deposited on mandrel 105. Other beams, such as beams 191 A-D, contain other isotopes or contaminants of source material 120 and these other beams are prevented from reaching mandrel 105 through use of templates 181 and 182.

Following deposition, the coated mandrel 105 is removed from the chamber 110. The top and bottom ends 107, 108 of the coated mandrel 105 are removed by any suitable means such as, for example, cutting with a low-speed cutting saw equipped with a diamond-impregnated copper cutting wheel. Alternatively, multiple cuts can be made of a relatively long coated mandrel to yield numerous coated mandrel portions, each of which is used to form a stent.

Figure 6A:
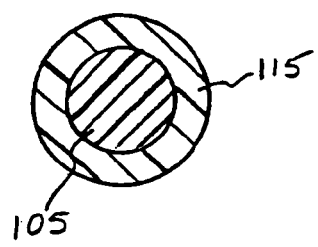
FIG. 6A depicts a cross sectional view of the substrate with a deposition layer of FIG. 5 taken along the 6-6 axis.
Figure 7:
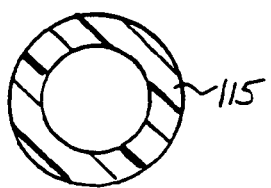
FIG. 7 shows the cross sectional view of deposition layer of FIG. 6 after removal of the substrate.

As depicted in FIG. 6A, which is a cross sectional view of the coated mandrel 105 taken along the 6-6 axis, the metallic layer 115 encompasses mandrel 105. To form a medical device or a member of a medical device the metallic layer 115 is removed from mandrel 105. The metallic layer 115 is removed from the coated mandrel 105 by any suitable technique such as, for example, exposing the coated mandrel 105 to a solution which will dissolve the mandrel material but not the metallic layer 115. As an example, when the mandrel 105 is a low carbon steel wire and the metallic layer 115 comprises nitinol, the mandrel 105 may be dissolved with a suitable acid, such as hydrochloric acid, which does not destroy the metallic layer 115 to form a medical device or member. FIG. 7 depicts a view of the metallic layer 115 of FIG. 6A after the mandrel 105 has been removed.

As an alternative, the metallic layer 115 may be removed from the mandrel 105 by machining techniques such as, for example, drilling, grinding, milling, laser cutting, laser milling and the like.

Figure 8:
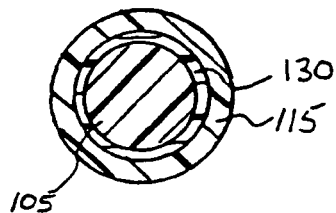
FIG. 8 shows a multi-layered substrate having a release layer, in accordance with another embodiment of the present invention.

As another alternative, a release layer 130 is formed between the mandrel 105 and the metallic layer 115 as shown in FIG. 8. The release layer 130 is applied to the mandrel 105 by any suitable coating technique such as, for example, dipping, spraying, rolling, electroplating, vapor deposition and the like. After deposition of the metallic layer II 5, the release layer 130 is removed by machining or, desirably, by dissolving it in a solution that attacks the material of the release layer 130 while not affecting the materials of the mandrel 105 and the metallic layer 115. For instance, sulfuric acid is a useful release agent when the mandrel is titanium or tantalum, the release layer is copper and the metallic layer is nitinol.

After release from the mandrel 105 or from the release layer 130, the metallic layer 115 either serves as a stent or as the basis for forming a stent by further processing. Desirably, a stent formed in accordance with the present invention will have a pattern of openings, such as openings 101 in slotted metallic stent, therein to help facilitate expansion for deployment within a body lumen. In one aspect, the openings 101 in the stent 100 are formed by machining such openings into the metallic layer 115 after removal from the mandrel 105.

Figure 9:
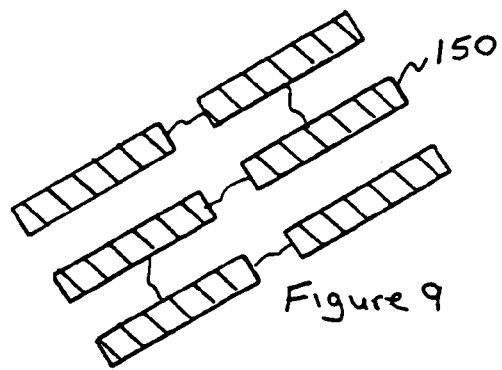
FIGS. 9 and 10 show side and end views, respectively, of an example of a deposition mask used in accordance with an embodiment of the present invention.
Figure 10:
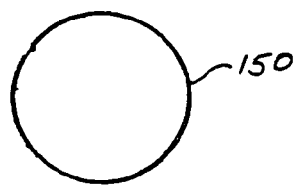

In another aspect, a mask 150 is used to surround the mandrel 105 during deposition of the metallic layer 115. FIGS. 9 and 10 show side and end views, respectively, of an example of the mask 150. The mask 150 is shaped as the inverse of the intended final stent configuration such that the vapor deposition process results in a pattern of openings, such as openings 101 in slotted metallic stent 100, in the metallic layer 15. A mask may also be suitably used to form other shapes or configurations, such as openings 210 in wire-formed metallic stent 200.

Figure 11:
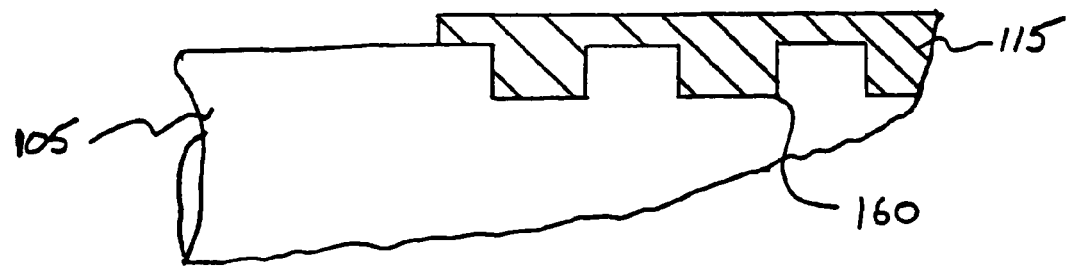
FIG. 11 shows a portion of a patterned substrate having a vapor deposited metallic layer, in accordance with an embodiment of the present invention.
Figure 12:
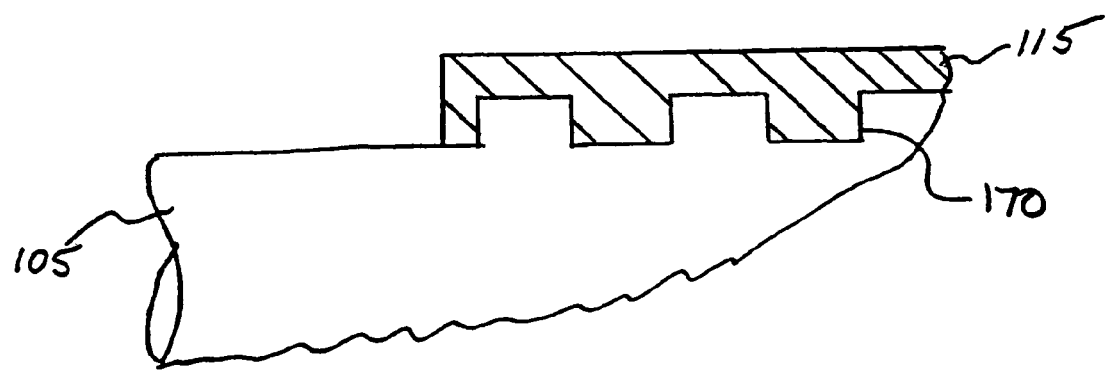
FIG. 12 shows a portion of a second patterned substrate having a vapor deposited metallic layer, in accordance with an embodiment of the present invention.
Figure 13:
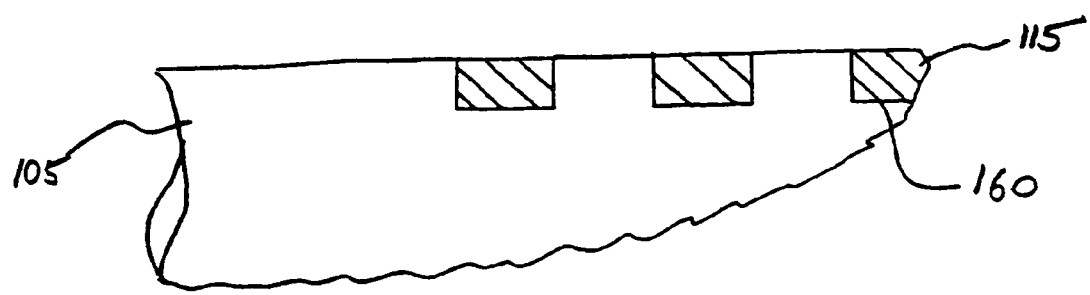
FIG. 13 shows a portion of the patterned substrate of FIG. 11 after removal of a portion of the metallic layer.

In yet another aspect, the mandrel 105, as illustrated in FIG. 11, is patterned to cause a corresponding pattern to be formed in the deposited metallic layer 115. FIG. 11 is a partial longitudinal view of coated mandrel 105 of FIG. 5 taken along the 11-11 axis. The pattern in the mandrel 105 may be, for example, a negative pattern 160 in which the intended pattern for stent 100 is recessed into the mandrel 105. Alternatively, the pattern in the mandrel 105 may be a positive pattern 170, as depicted in FIG. 12, in which the intended pattern for stent 100 is extended from the mandrel 105. Negative patterns, positive patterns or combinations thereof may be used with the present invention. As depicted in FIG. 13, portions of the metallic layer 115 not intended to be part of the stent 100 is removed by any suitable process such as, for example, machining, etching, laser cutting and the like to form a medical device or a member of a medical device. The remaining portions of the metallic layer 115 in FIG. 13 may be removed from the mandrel 105 by use of the aforementioned methods of the present invention.

The positive and negative patterns on the mandrel are configured to produce a reverse image of the stent on the surface of the mandrel. Machinery for producing the reverse image on the surface of the mandrel may vary depending on the complexity of the geometric pattern, type of material used for the mandrel and other considerations. Fine cutting heads or tools may be used to machine a pattern into the mandrel with micro-machining methods. Etching, molding and lase ring techniques are also useful methods for forming the reverse image on the mandrel.

The reverse image which is formed on the surface of the mandrel is desirably free or substantially free from micropores or defects because the quality of the subsequently vapor deposited stent may depend, in part, on the surface quality. Thus, subsequent to the mechanical formation of the reverse image, chemical etching or other polishing techniques may be used to remove surface imperfections. Additionally, oils, oxides and other matter which may interfere with the quality of the vapor-deposited metallic layer are removed prior to the vapor deposition. Chemical and electrochemical cleaning may be used to so condition the surface of the micro-machined mandrel.

Figure 14:
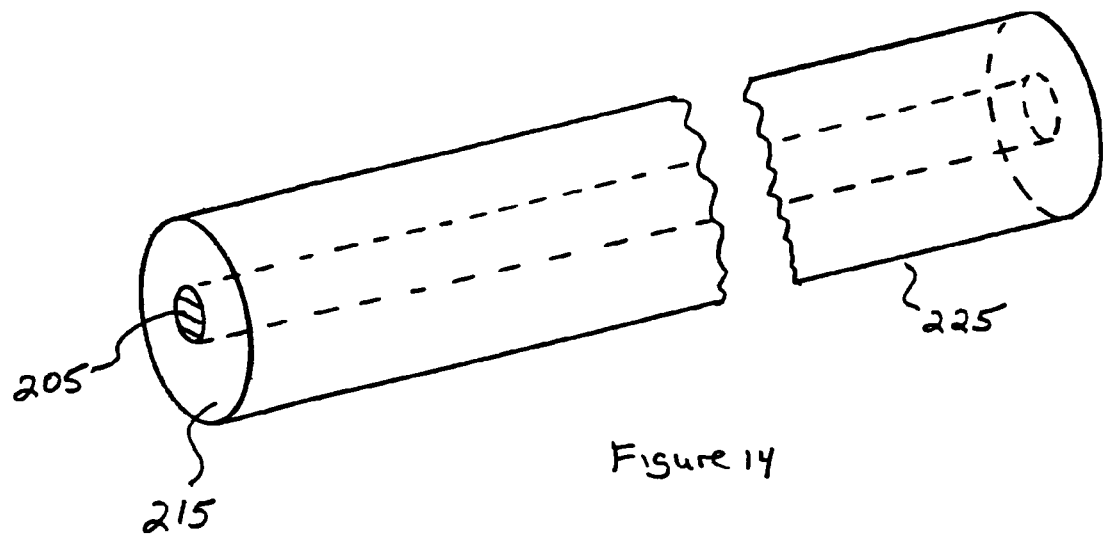
FIG. 14 shows a stent wire for use in forming the medical device of FIG. 3, in accordance to an embodiment of the present invention.
Figure 15:
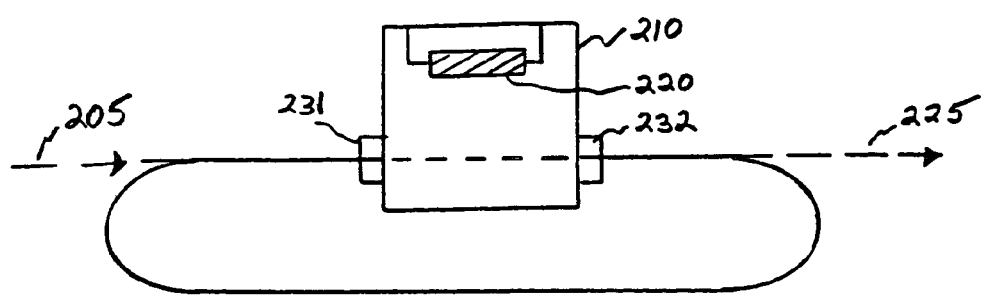
FIG. 15 shows an example of a vapor deposition apparatus for forming the stent wire of FIG. 14, in accordance with an embodiment of the present invention.

In another aspect of the present invention, a fine metal wire may be used as the target for vapor deposition. As depicted in FIGS. 14 and 15, metallic layer 215 is deposited onto wire 205 with vapor deposition methods of the present invention to form stent wire 225. Wire 205 is introduced into vacuum chamber 210 through seal 231. Source material 20 is deposited by vapor deposition onto wire 205. The coated wire 205 exits vacuum chamber 210 through seal 232 seals 231 and 232 serve to maintain vacuum conditions within vacuum chamber 210 as wire 205 is passed through vacuum chamber 210.

As depicted in FIG. 15, wire 205 can be cycled through vacuum chamber 210 through multiple passes until a desire thickness of metallic layer 215 is obtained. After achieving the desired thickness of metallic layer 215, stent wire 225 may removed from the vapor deposition process to form wire-formed metallic stent 200, or other medical device. Stent wire 225 can be formed into stent 200 by appropriate bending and attaching, such as welding, techniques.

Metallic layer 215 can be fabricated as a single crystal material, monocrystalline and monoisotopic material or a nanocrystalline material by previously described inventive methods. Desirably, stent wire 225 has a single crystal structure.

The material deposited as the metallic layer 115 or 215 is any suitable material for use in medical device applications such as, for example, nitinol, stainless steel, titanium, cobalt-chromium alloys, gold, platinum, niobium, zirconium, silver, tantalum and alloys thereof. The vapor deposition of these materials results in a deposited metallic layer 115 having a fine, equiaxed microstructure which may be precisely established as a function of process parameters. These microstructures in turn affect mechanical properties such as strength and corrosion resistance.

Figure 6B:
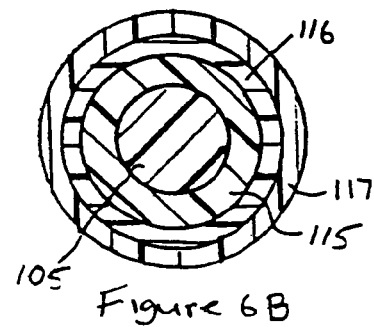
FIG. 6B shows a multi-layered substrate, in accordance with another embodiment of the present invention.

The process of the present invention is further amenable to the deposition of multiple layers for the further improvement of desired medical device properties. For example, as depicted in FIG. 6B, the deposited metallic layer 115 is optionally coated with a layer 116 of a radiopaque material such as platinum or tantalum to impart radiopacity to the medical device. The deposited metallic layer 115 is also optionally coated with a layer 117 of a material, such as carbon, to impart thrombogenicity and corrosion and/or fatigue resistance to the medical device. If applied to the metallic layer 115, such additional coatings 116, 117 are applied singularly or in any combination. Moreover, the additional coatings 116, 117 are desirably applied in the same vacuum chamber 110 used for the deposition of metallic layer 115. To facilitate the deposition of the additional coatings 116, 117, it is preferred that the chamber 110 be equipped to receive and deposit multiple sources so that the additional coatings 116, 117 can be deposited immediately following the deposition of metallic layer 115 without breaking vacuum. Alternatively, the source materials for the additional coatings 116, 117 may be sequentially loaded into the chamber 110 for deposition.

Following the deposition of the metallic layer 115 and optional layers 116, 117, the coated mandrel 105 is removed from the chamber 105. The layers 115, 116, 117 are optionally subjected to further processing steps such as, for example, machining, heat treating, oxidizing, welding, attaching to other components, applying organic coatings, and the like. If the layer 115 comprises nitinol or another shape memory alloy, it is subjected to thermomechanical "training" steps to induce the shape memory effect, as is known in the art.

The present invention is further described with reference to the following non-limiting examples.

EXAMPLES

Example 1

A patterned nitinol stent is formed according to the following processing steps. A steel wire mandrel measuring about 10 mm in diameter and 30 mm in length is placed in a vacuum chamber on a motor driven rotary mount. Also mounted in the chamber is a nitinol source target comprising about 55.9 wt % nickel and the balance essentially titanium. The chamber is then evacuated to a pressure of less than $10^{-6}$ torr. Argon is introduced into the chamber at a flow rate of 100 cm$^3$/min, producing an operating pressure of about 10 millitorr. A plasma is then generated in the chamber by ion bombardment of the nitinol target, resulting in nitinol deposition onto the wire mandrel. Sputter deposition is continued until the thickness of the deposited nitinol layer is about 0.25 mm, after which the coated mandrel is removed from the chamber.

The coated mandrel is cut at both ends to a length of about 20 mm. A pattern is formed in the coated mandrel by machining oval-shaped holes through the thickness thereof. The deposited nitinol layer is removed from the mandrel by dissolving the mandrel in hydrochloric acid thus yielding a functional nitinol stent with a fine, equiaxed and nanocrystalline microstructure. The grain size of the nanocrystalline structure can be measured by a number of suitable techniques. A useful technique includes transmission electron microscopy to measure grain sizes at multiple grain boundaries with computer averaging of the measured results. A grain size of the nanocrystalline structure is measured to be less than 10 nanometers by this technique.

Example 2

A patterned nitinol stent is formed according to the following processing steps. A steel wire mandrel measuring about 10 mm in diameter and 30 mm in length is placed in a vacuum chamber on a motor driven rotary mount. The mandrel is machined prior to deposition to reflect the desired stent pattern. Specifically, the mandrel is machined to include slots measuring about 2 mm in length and 1 mm in width. Also mounted in the chamber is a nitinol source target comprising about 55.9 wt % nickel and the balance essentially titanium. The chamber is then evacuated to a pressure of less than $10^{-6}$ torr. Argon is introduced into the chamber at a flow rate of 100 cm$^3$/min, producing an operating pressure of about 10 millitorr. A plasma is then generated in the chamber by ion bombardment of the nitinol target, resulting in nitinol deposition onto the wire mandrel. Sputter deposition is continued until the thickness of the deposited nitinol layer is about 0.25 mm, after which the coated mandrel is removed from the chamber. After deposition, the deposited nitinol layer is patterned due to the pattern of the underlying mandrel.

The coated mandrel is cut at both ends to a length of about 20 mm. The deposited nitinol layer is removed from the mandrel by dissolving the mandrel in hydrochloric acid. After dissolving the mandrel, the interior of the stent is machined by laser milling to remove residual nitinol that had been deposited on the mandrel walls that defined the slots. The result is a patterned nitinol stent with a fine, equiaxed nanocrystalline microstructure. The grain size of the nanocrystalline structure is measured to be less than 10 nanometers by transmission electron microscopy with computer averaging.

Example 3

A patterned nitinol stent is formed according to the following processing steps. A steel wire mandrel measuring about 10 mm in diameter and 30 mm in length is placed in a vacuum chamber on a motor driven rotary mount. A cylindrical mask is used to surround the mandrel during deposition to form a pattern in the deposited nitinol layer. The mask is configured so as to result in the deposition layer with oval-shaped openings therein, the openings measuring about 2 mm in length and 1 mm in width. Also mounted in the chamber is a nitinol source target comprising about 55.9 wt % nickel and the balance essentially titanium. The chamber is then evacuated to a pressure of less than $10^{-6}$ torr. Argon is introduced into the chamber at a flow rate of 100 cm$^3$/min, producing an operating pressure of about 10 millitorr. A plasma is then generated in the chamber by ion bombardment of the nitinol target, resulting in nitinol deposition onto the wire mandrel. Sputter deposition is continued until the thickness of the deposited nitinol layer was about 0.25 mm, after which the coated mandrel is removed from the chamber.

The coated mandrel is cut at both ends to a length of about 20 mm. The deposited nitinol layer is removed from the mandrel by dissolving the mandrel in hydrochloric acid thus yielding a patterned nitinol stent with a fine, equiaxed nanocrystalline microstructure. The grain size of the nanocrystalline structure is measured to be less than 10 nanometers by transmission electron microscopy with computer averaging.

Example 4

A patterned nitinol stent is formed according to the following processing steps. A steel wire mandrel measuring about 10 mm in diameter and 30 mm in length is placed in a vacuum chamber on a motor driven rotary mount. Also mounted in the chamber are the following source materials: a nitinol source target comprising about 55.9 wt % nickel and the balance essentially titanium; and a platinum source target. The chamber is then evacuated to a pressure of less than $10^{-6}$ torr. Argon is introduced into the chamber at a flow rate of 100 cm$^3$/min, producing an operating pressure of about 10 millitorr. A plasma is then generated in the chamber by ion bombardment of the nitinol target, resulting in nitinol deposition onto the wire mandrel. Sputter deposition is continued until the thickness of the deposited nitinol layer is about 0.25 mm, after which the platinum is sputter deposited to a thickness of about 0.1 mm. The coated mandrel is then removed from the chamber.

The coated mandrel is cut at both ends to a length of about 20 mm. A pattern is formed in the coated mandrel by machining oval-shaped holes through the thickness thereof. The deposited nitinol layer is removed from the mandrel by dissolving the mandrel in hydrochloric acid thus yielding a patterned nitinol stent with a fine, equiaxed nanocrystalline microstructure and a radiopaque platinum coating. The grain size of the nanocrystalline structure is measured to be less than 10 nanometers by transmission electron microscopy with computer averaging.

Example 5

A patterned nitinol stent is formed according to the following processing steps. A steel wire mandrel measuring about 10 mm in diameter and 30 min in length is placed in a vacuum chamber on a motor driven rotary mount. Also mounted in the chamber are the following source materials: a nitinol target comprising about 55.9 wt % nickel and the balance essentially titanium; a platinum source target; and a carbon source target. The chamber is then evacuated to a pressure of less than $10^{-6}$ torr. Argon is introduced into the chamber at a flow rate of 100 cm$^3$/min, producing an operating pressure of about 10 millitorr. A plasma is then generated in the chamber by ion bombardment of the nitinol target, resulting in nitinol deposition onto the wire mandrel. Sputter deposition is continued until the thickness of the deposited nitinol layer is about 0.25 mm, after which the platinum is sputter deposited to a thickness of about 0.1 mm. Following platinum deposition, the carbon source is evaporated by electron beam interaction. The coated mandrel is then removed from the chamber.

The coated mandrel is cut at both ends to a length of about 20 mm. A pattern is formed in the coated mandrel by machining oval-shaped holes through the thickness thereof. The deposited nitinol layer is removed from the mandrel by dissolving the mandrel in hydrochloric acid thus yielding a patterned nitinol stent with a fine, equiaxed nanocrystalline microstructure and a radiopaque platinum coating. The grain size of the nanocrystalline structure is measured to be less than 10 nanometers by transmission electron microscopy with computer averaging.

In the foregoing the invention has been described by means of specific embodiments, but it will be understood that various changes and modifications may be performed without deviating from the scope and spirit of the invention.

What is claimed is:

1. An implantable medical device comprising one or more biocompatible metallic members arranged to form a radially deformable tubular member, at least one of the biocompatible metallic members consisting of a biocompatible metal having a morphology defined by grain sizes having a maximum dimension of between 1 nanometer and 10 nanometers, wherein said device is a stent.

2. The device of claim 1, wherein said one or more members is further defined by an orderly grain structure with substantially similar crystal orientation.

3. The device of claim 1, wherein said one or more members is selected from the group of biocompatible metals consisting of nitinol, platinum, titanium, nickel, gold, niobium, zirconium, silver, tantalum, cobalt, chromium, stainless steel, and alloys thereof.

4. The device of claim 1, wherein said one or more members is an alloy of biocompatible metals defined by an orderly grain structure with substantially similar crystal orientation, said metals selected from the group consisting of nitinol, platinum, titanium, nickel, gold, niobium, zirconium, silver, tantalum, cobalt, chromium, stainless steel, and alloys thereof.

5. A stent consisting of a tubular member comprising a plurality of slots, the tubular member comprising nitinol having a morphology defined by grain sizes having a maximum dimension of between 1 nanometer and 10 nanometers.

6. The stent of claim 5, wherein the tubular member consists of nitinol having a morphology defined by grain sizes of less than 10 nanometers.

7. The stent of claim 5, wherein the tubular member further comprises a radiopaque coating overlying the nitinol.

8. The stent of claim 7, wherein the radiopaque coating comprises platinum.

* * * * *